US006903196B1

(12) United States Patent
Roben et al.

(10) Patent No.: US 6,903,196 B1
(45) Date of Patent: Jun. 7, 2005

(54) METHODS FOR IDENTIFYING AND ISOLATING TISSUE-SPECIFIC LUMEN-EXPOSED MOLECULES

(75) Inventors: Paul Roben, San Diego, CA (US); Anthony C. Stevens, San Diego, CA (US)

(73) Assignee: Utah Ventures II, L.P., Salt Lake City, UT (US)

( * ) Notice: Subject to any disclaimer, the term of this patent is extended or adjusted under 35 U.S.C. 154(b) by 0 days.

(21) Appl. No.: 09/528,742

(22) Filed: Mar. 20, 2000

Related U.S. Application Data
(60) Provisional application No. 60/139,579, filed on Jun. 17, 1999.

(51) Int. Cl.[7] .............................. A23J 1/00; C07K 1/00; A01N 1/00; G01N 33/543
(52) U.S. Cl. ......................... 530/412; 435/1.1; 436/518
(58) Field of Search ........................ 436/518; 530/412; 435/1.1

(56) References Cited

U.S. PATENT DOCUMENTS

| | | | |
|---|---|---|---|
| 5,218,700 A | 6/1993 | Beechick | |
| 5,610,008 A | 3/1997 | Schnitzer et al. | |
| 5,660,827 A | 8/1997 | Thorpe et al. | |
| 5,776,427 A | 7/1998 | Thorpe et al. | |
| 5,776,770 A | 7/1998 | Schnitzer et al. | |
| 5,855,866 A | 1/1999 | Thorpe et al. | |
| 5,914,127 A | 6/1999 | Schnitzer et al. | |
| 5,914,312 A | 6/1999 | Axworthy et al. | |
| 5,948,624 A | * 9/1999 | Rothschild et al. | ............ 435/6 |
| 5,965,132 A | 10/1999 | Thorpe et al. | |
| 5,994,519 A | 11/1999 | Osbourn et al. | |
| 6,004,554 A | 12/1999 | Thorpe et al. | |
| 6,068,829 A | 5/2000 | Ruoslahti et al. | |
| 6,136,311 A | 10/2000 | Bander | |

FOREIGN PATENT DOCUMENTS

| | | |
|---|---|---|
| WO | WO97/04748 | 2/1997 |
| WO | WO 98/39469 | 9/1998 |
| WO | WO 00/07625 | 2/2000 |
| WO | WO01/71359 | 9/2001 |

OTHER PUBLICATIONS

Pierce Chemical Company, 1994, 2600002 94CAT, Pierce Life Science & Analytical Research Products Catalog & Handbook.*

Chen, et al. 1998, Determination of external loop topology in the serotonin transporter by site–directed chemical labeling, *Journal of Biological Chemistry*, 273(20):12675–12681.

Kandror, et al. 1999, Insulin regulation of protein traffic in rat adipose cells. *Journal of Biological Chemistry*, 274(36):25210–25217.

Mouton, et al. 1982. A reagent for covalently attaching biotin to proteins via a cleavable connector arm. *Archives of Biochemistry*, 218(1):101–108.

International Search Report from co–pending PCT/US01/08705 dated May 21, 2002.

Huwyler et al, "Brain Drug Delivery of Small Molecules Using Immunoliposomes", Proc. Natl. Acad. Sci. USA, Nov. 1996, vol. 93, pp. 14164014164.

Huwyler et al, "Receptor Mediated Delivery of Daunomycin Using Immunoliposome: Oharmacokinetics and Tissue Distribution in the Rat", The Journal of Pharmacology and Experimental Therapeutics, 1997, vol. 282, No. 3, pp. 1541–1546.

Hastie et al., Identification of Surface Components of Mammalian Respiratory Tract Cilia *Cell Motility and the Cytoskeleton* 17:317–328 (1990).

Schnitzer et al., Separation of Caveolae from Associated Microdomains of GPI–Anchored Proteins *Science* 269:1435–1439 (Sep. 1995).

Dentler William L., Nonradioactive Methods for Labeling and Identifying Membrane Surface Proteins *Methods in Cell Biology* 47:407–411 (1995).

Schnitzer et al., Caveolae from luminal plasmalemma of rat lung endothelium: Microdomains enriched in caveolin, $Ca^{2+}$–ATPase, and inositol trisphosphate receptor *Proc. Natl. Acad. Sci.* 92:1759–1763 (Feb. 1995).

Dentler, William L., Identification of *Tetrahymena* Ciliary Surface Proteins Labeled with Sulfosuccinimidyl 6–(Biotinamido) Hexanoate and Concanavalin A and Fractionated with Triton X–114 *J. Protozool.* 39(3):368–378 (May–Jun. 1992).

Levy–Toledano et al. Streptavidin Blotting: A Sensitive Technique to Study Cell Surface Proteins; Application to Investigate Autophosphorylation and Endocytosis of Biotin–Labeled Insulin Receptors *Endocrinology* 133(4):1803–1808 (Oct. 1993).

Bush et al., Selective isolation of individual cell surface proteins from tissue culture cells by a cleavable biotin label *European Journal of Cell Biology* 50:257–262 (Dec. 1989).

De La Fuente et al., Biotinylation of membrane proteins accessible via the pulmonary circulation in normal hyperoxic rats *Am. J. Physiol.* 272(3) Part 1:L461–L470 (Mar. 1997).

(Continued)

Primary Examiner—Joseph Woitach (57) ABSTRACT

This invention provides novel methods of and kits for labeling and isolating lumen-exposed molecules, particularly polypeptides which are expressed in a tissue-specific or organ-specific manner. The methods and kits can be used to isolate molecules exposed on the luminal side of cells lining vascular, ductal, sinus, respiratory, fascial, and other perfusible tissue spaces.

45 Claims, 5 Drawing Sheets

OTHER PUBLICATIONS

Garlanda et al., Heterogeneity of Endothelial Cells *Arteriosclerosis, Thrombosis and Vascular Biology* 17(7):1193–1202 (Jul. 1997).

Lamszus et al., Isolation and Culture of Human Neuromicrovascular Endothelial Cells for the Study of Angiogenesis In Vitro *Journal of Neuroscience Research* 55:370–381 (Feb. 1999).

Craig et al., Endothelial Cells from Diverse Tissues Exhibit Differences in Growth and Morphology *Microvascular Research* 55:65–76 (Jan. 1998).

Pasqualini, R., Vascular targeting with phage peptide libraries *The Quarterly Journal of Nuclear Medicine* 43(2):159–162 (Jun. 1999).

Pasqualini et al., Organ targeting in vivo using phage display peptide libraries *Nature* 380(28):364–366 (Mar. 1996).

Rajotte et al., Molecular Heterogeneity of the Vascular Endothelium Revealed by In Vivo Phage Display *Journal of Clinical Investigation* 102(2):430–437 (Jul. 1998).

* cited by examiner

Figure 1

Profiles of luminally-exposed vascular membrane proteins from 6 different tissues.

Figure 2

Brain Kidney  Brain Kidney

Mild Elution

Harsh Elution

PECAM-1

Golgi 58Kda

Fig 3B

Golgi 58KDa in Original Tissues

Figure 4

1-D Electrophoresis

A

Western Blot

METHODS FOR IDENTIFYING AND ISOLATING TISSUE-SPECIFIC LUMEN-EXPOSED MOLECULES

This application claims priority to U.S. Provisional Patent Application No. 60/139,579, filed Jun. 17, 1999.

TECHNICAL FIELD

This invention generally pertains to the field of vascular biology and medicine. In particular, this invention provides novel methods and kits for labeling and isolating lumen-exposed molecules, particularly polypeptides which are expressed in a tissue-specific or organ-specific manner. The methods and kits can be used to isolate molecules exposed on the luminal side of cells lining vascular, ductal, sinus, respiratory, fascial, and other perfusible tissue spaces.

BACKGROUND

Currently, when drugs are conventionally administered to a patient, they circulate throughout the entire body of the patient. As a result, extremely high dosages are required to reach therapeutic levels in the desired organ. This non-targeted delivery of high dosages of drugs results in systemic toxicity and severe side-effects.

Targeted delivery of therapeutic or diagnostic agents to specific organs or tissues is much safer and more effective than delivery of a drug to an entire individual, as is the case by conventional administration techniques. The ability to specifically deliver a composition (e.g., a drug or gene) to a specific organ or tissue in vivo allows much smaller amounts of the drug to be administered thereby reducing associated side effects.

Conventional means to achieve this sort of "targeted" or organ-specific delivery includes the use of implants (e.g., Elisseeff (1999) Proc. Natl. Acad. Sci. USA 96:3104–3107), stents or catheters (see, e.g., Murphy (1992) Circulation 86:1596–1604), or vascular isolation of an organ (e.g., liver, see, e.g., Vahrmeijer (1998) Semin. Surg. Oncol. 14:262–268). However, these techniques are invasive, traumatic and can cause extensive inflammatory responses and fibrocellular proliferation (see, e.g., van der Giessen (1996) Circulation 94:1690–1697).

A more sophisticated strategy is the targeted delivery of compounds to organ- or tissue-specific molecules exposed on the luminal surface of the vasculature. Previous attempts at tissue-specific delivery depended on sites within the tissue that were inaccessible to the compounds due to the natural barrier of the vasculature. Hence the importance of identifying accessible, tissue-specific molecules on the luminal surface of the vasculature. For example, vasculature-targeted chemotherapy, i.e., the destruction of tumor blood vessels with cytotoxic agents, makes use of biochemical differences between angiogenic and resting blood vessels (see, e.g., Ruoslahti (1999) Adv. Cancer Res. 76:1–20). This approach may minimize or eliminate some of the problems associated with conventional solid-tumor targeting, such as poor tissue penetration and drug resistance. Eliminating tumor blood supply using anti-angiogenic agents can have dramatic anti-tumor effects. Targeting chemotherapeutic agents to the tumor vasculature kills tumor blood vessels in addition to having the usual anti-tumor activities of the drug. This approach can result in increased efficacy and reduced toxicity of anti-tumor agents.

However, the versatility and scope of any biochemical targeting strategy is dependent on the in vivo or in situ identification of organ- or tissue-specific molecules as expressed on the luminal surface of the vasculature. One strategy is to identify organ-specific molecular differences in vivo is by screening peptide libraries expressed on the surface of bacteriophage (see, e.g., Rajotte (1998) J. Clin. Invest. 102:430–437). This method, though, will miss many potential tissue-specific molecules because it is dependent on the ability of fusion proteins to bind to cell surface molecules with sufficient affinity to isolate such molecules.

Another strategy is to selectively radioiodinate lumen-expressed polypeptides in situ. (see, e.g., Schnitzer (1990) Eur. J. Cell Biol. 52:241–251). However, this method is limited because it only labels polypeptides containing tyrosine residues and does not facilitate isolating the labeled molecule.

Another approach coats lumen-exposed cells with cationized silica particles followed by polyanion crosslinkers, in situ. (see, e.g., Schnitzer, et al., U.S. Pat. Nos. 5,281,700; 5,776,770; 5,914,127). The tissue is then homogenized and cell membranes bound to the silica are isolated by density gradients. This method, though, results in a significant fraction of non-lumen-expressed molecules contaminating the isolated fraction. In the Schnitzer-silica particle technique, once the cells are homogenized, all intracellular molecules can bind to the silica-polyanion complex. When whole membranes are isolated with this technique, molecules not exposed to the luminal surface are also isolated.

Another approach used in situ was to label isolated lungs by perfusing the pulmonary artery with the non-cleavable cell membrane impermeant biotinylation reagent sulfosuccinimidyl 6-biotin-amido hexanoate, which labels amine groups of polypeptides (De La Fuente (1997) Amer. J. of Physiol. 272:L461–L470). Tissue homogenates were incubated with strepavidin-agarose beads. To elute biotinylated polypeptides from the strepavidin harsh conditions were used because the affinity between biotin and avidin is about $10^{-15}$ $M^{-1}$. This resulted in significant contamination with non-specifically binding polypeptides and other non-lumen exposed molecules in the eluate. This method is also flawed in that significant amounts of naturally biotinylated proteins not normally exposed to the lumen in vivo are also isolated.

Because of the increased demand for use of more sophisticated drug delivery techniques, such as the biochemical strategy of targeted delivery of drugs and genes only to organ- or tissue-specific molecules, different ways of identifying and isolating such molecules are needed. The present invention addresses these and other needs.

SUMMARY

This invention provides novel methods and kits to label and isolate lumen-exposed molecules, particularly polypeptides that are expressed in a tissue-specific or organ specific manner on the luminal side of cells lining vascular, ductal and other perfusible tissue spaces.

The invention provides methods for labeling and isolating molecules exposed to perfusible spaces, particularly tissue-specific and organ-specific molecules. Alternatively, the methods can be used to identify and isolate molecules expressed only under certain conditions, e.g., at particular stages of development or aging (e.g., "senescent endothelial cells," see, e.g., Garlanda (1997) Arterioscler. Thromb. Vasc. Biol. 17:1193–1202), after exposure to particular hormones or cytokines (e.g., lymphokines), in inflamed, infected, or diseased tissues, molecules preferentially expressed on one or more tissues, or the like. Lumen-exposed molecule preparations from different tissues are compared to identify the conditionally expressed molecule (e.g., compare tissues isolated before and after exposure to molecule, injury, infectious agent, and the like).

The molecules to be "tagged" (and thus labeled and/or isolated) can be directly attached to the membrane or cells lining the perfusible space or they can be indirectly attached, as, e.g., extracellular matrix molecules, or, deposits or buildups present only in certain pathologic, inflammatory, or infectious conditions or at particular stages of development. The molecules that can be "tagged" include all lumen-exposed molecules, including, e.g., polypeptides, lipids, carbohydrates (e.g., polysaccharides), nucleic acids, and the like.

In one embodiment, the invention provides a method of labeling a molecule (e.g., organ-specific or tissue-specific molecules) exposed on a luminal surface of a perfusible space in situ or in vivo, or any intact organ or tissue in contact with a perfusible space. The method comprises (a) providing a cell membrane impermeable reagent comprising three (or more) domains; (i) a first domain comprising a chemical moiety capable of covalently and non-specifically binding to a molecule exposed on the luminal surface of a cell or tissue (including extracellular matrix, connective tissue, and the like) lining a perfusible space in situ or in vivo, (ii) a second domain comprising a labeling or detectable domain, and (iii) a third domain situated between the first and second domains linking the first domain to the second domain by a cleavable chemical moiety, wherein the cleavable chemical moiety will not cleave under in vivo conditions; and, (b) administering the membrane impermeable reagent into the perfusible space in an intact tissue or intact organ or intact animal to react the cell membrane impermeable reagent with the molecule expressed on the luminal surface of the cell or tissue lining the perfusible space to label the lumen-exposed molecule (e.g., an organ-specific or a tissue-specific molecule).

In the methods of the invention, the perfusible space can be a lumen of a vascular vessel. The cell lining the perfusible space can be an endothelial cell or an epithelial cell. The vascular vessel can be an artery, an arteriole, a vein, or a capillary. The perfusible space can also be a lumen of a cerebral spinal fluid (CSF) space. The perfusible space can also be a lumen of a lymphatic vessel, an endocrine or exocrine duct or pore, or equivalent.

All lumen-exposed molecules directly or indirectly associated with tissues, cells and organs in contact with a perfusible space are targets for "tagging" (detection or labeling) and isolation in the methods of the invention. In alternative embodiments, the organ is, or the tissue is derived from, e.g., a heart, a lung, a brain, a liver, a kidney, an endocrine gland, the CNS, skin, a reproductive organ, a digestive tract organ, or an eye, to name just a few.

The labeling domain can be any molecular composition that is detectable (directly or indirectly) or that is capable of specifically binding to a second composition (which can be immobilized, e.g., on a bead). In alternative embodiments, the labeling domain of the reagent is a polypeptide (e.g., a ligand or epitope), a nucleic acid or a peptide nucleic acid (PNA) (e.g., capable of specifically hybridizing to its complementary sequence), a fluorescent molecule, a colorimetric agent, a radionuclide, a naturally occurring or a synthetic organic molecule or a chelate. For example, the polypeptide can be a polyhistidine.

The cleavable chemical moiety can be any chemical moiety that will not cleave under in vivo conditions. In one embodiment, the second domain's cleavable moiety is cleavable under relatively mild conditions. For example, exemplary mild conditions include, e.g., non-denaturing conditions, comprising, e.g., approximately physiologic pH, about 22° C. to 37° C., physiologic salt conditions, or equivalent conditions. For example, when the cleavable domain is a disulfide group, an exemplary set of mild conditions comprises use of about 10 mg/ml dithiothreitol (DTT) for about 1 to 2 minutes at about room temperature in a solution equivalent to physiologic salt conditions (to be used if the cleavable moiety is a disulfide, or equivalent, group). In alternative embodiments, the cleavable chemical moiety is a periodate-cleavable glycol, a dithionite-cleavable diazobond, a hydroxylamine-cleavable ester or a base-labile sulfone. The cleavable chemical moiety also can be any chemical entity cleavable by an enzymatic reaction, e.g., a nucleic acid (e.g., an oligonucleotide) that is cleavable by a restriction enzyme, or a peptide domain cleavable by an enzyme, e.g., an endopeptidase.

In an alternative embodiment, where the second domain comprises a labeling or detectable domain, the cell membrane impermeable reagent can further comprise a fourth domain comprising a binding domain.

In one embodiment, the methods comprise administering the cell membrane impermeable reagent directly into the perfusible space of the intact organ or tissue or the intact animal, e.g., by administration of a buffered, aqueous solution comprising the cell membrane impermeable reagent into the perfusible space.

The invention also provides methods of isolating a molecule, e.g., an organ-specific or tissue-specific molecule, that is exposed on a luminal surface of a perfusible space comprising the following steps: (a) providing a cell membrane impermeable reagent comprising three domains (i) a first domain comprising a chemical moiety capable of covalently and non-specifically binding to a molecule expressed on the luminal surface of a cell lining a perfusible space in situ or in vivo, (ii) a second domain comprising a binding domain, and (b) administering the cell membrane impermeable reagent into the perfusible space in an intact organ or an intact animal to react the cell membrane impermeable reagent with a molecule expressed on the luminal surface of the cell lining the perfusible space; and (c) isolating the reagent-reacted molecule. In one embodiment, the method can further comprise the step of comparing the reagent-reacted molecules from different organs or tissues to identify an organ-specific or tissue-specific molecule, wherein the organ-specific or tissue-specific molecule is exposed on the luminal surface of the perfusible space of only one of the compared organs or tissues. Alternatively, the method can further comprise comparing reagent-reacted molecules from the different tissue states (e.g., at different stages of development or aging, before and after exposure to particular hormones or cytokines, or insults, or drugs, or injury, or in inflamed, infected, or diseased tissues, or the like), the comparison identifying a "stage"- or "reaction"-specific molecule, wherein this molecule is exposed only on the luminal surface of the perfusible space of a tissue or organ from one of the compared stages or states.

In alternative embodiments, the perfusible space is a lumen of a vascular vessel and the cell lining the space is an endothelial cell. The vascular vessel can be an artery, an arteriole, a vein, or a capillary. The perfusible space can be a lumen of a cerebral spinal fluid (CSF) space. The perfusible space an be a lumen of a lymphatic vessel and the cell lining the space is an endothelial cell. The perfusible space can be a lumen of an endocrine or exocrine duct or pore. The cell lining the perfusible space can be an epithelial cell. The organ can be, or the tissue can be derived from, for example, a heart, a lung, a brain, a liver, a kidney, an endocrine gland, skin, a reproductive organ, a digestive tract organ, or an eye.

As noted above, the binding domain of the reagent can be a biotin, a polypeptide, a nucleic acid, a peptide nucleic acid, a naturally occurring or a synthetic organic molecule or a chelate. The polypeptide can be a polyhistidine.

Also as discussed above, the cleavable chemical moiety can be a disulfide group, a periodate-cleavable glycol, a dithionite-cleavable diazobond, a hydroxylamine-cleavable ester or a base-labile sulfone.

In an alternative embodiment, where the second domain comprises a binding domain, the cell membrane impermeable reagent can further comprises a fourth domain comprising a molecule that facilitates detection (e.g., labeling or imaging) of the reagent. The fourth domain molecule that facilitates detection can comprise any detectable molecule, e.g., a fluorescent molecule, a calorimetric agent or a radionuclide.

The methods of the invention can also comprise administering the cell membrane impermeable reagent into the perfusible space of the intact organ or tissue or the intact animal by administration of a buffered, aqueous solution comprising the cell membrane impermeable reagent. Concentrations of reagent can vary under the circumstances, e.g., from about 0.5 to about 10 mg/ml; optimal buffers and dosages can be determined by routine methods. In one embodiment, two separate cell membrane impermeable reagents are co-administered.

As discussed above, any molecules exposed on the luminal surface of the perfusible space can be identified and isolated by the cell membrane impermeable reagent. These "tagged" and isolated molecules can be, e.g., a polypeptide, a lipid, a carbohydrate (e.g., polysaccharide) or the like.

In one embodiment, the reagent-reacted molecule is isolated by (a) contacting a cell or a membrane isolate or a cell or a tissue homogenate or an extract derived from the reagent-reacted organ or animal with a ligand having affinity for the binding domain of the cell membrane impermeable reagent; and (b) removing a non-bound molecule from the ligand-bound fraction, or, by removing substantially all of the non-bound molecules from the ligand-bound fraction. The non-bound molecule can be removed by washing or by electrophoresis, or the like.

In various embodiments, the ligand is immobilized, e.g., on a bead, membrane, a gel, a fiber, or the like. The binding domain is a biotin the binding domain ligand can an avidin or a strepavidin molecule.

The reagent-reacted molecule can be further isolated by cleavage of the cleavable chemical moiety of the cell membrane impermeable reagent after removing a non-bound molecule, some non-bound molecules or substantially all non-bound molecules. The conditions for cleaving the cleavable chemical moiety do not dissociate the binding domain from the ligand. In one embodiment, the conditions for cleaving the cleavable chemical moiety do not denature the reacted and isolated molecule. As discussed above, the conditions for cleaving the chemical moiety can comprise mild reducing, non-denaturing conditions.

After cleavage of the cleavable chemical moiety, the reagent-reacted molecule can be further isolated by elution from the binding domain and the ligand.

A method of isolating an organ-specific or tissue-specific molecule that is exposed on a luminal surface of an arteriole, a capillary or a vein comprising the following steps: (a) providing a cell membrane impermeable reagent comprising three domains (i) a first domain comprising an active moiety capable of covalently and non-specifically binding to a molecule expressed on the luminal surface of a cell lining a perfusible space in situ or in vivo, (ii) a second domain comprising a biotin binding domain, and (iii) a third domain comprising a disulfide moiety situated between the first and second domains linking the first domain to the second domain; and, (b) administering the cell membrane impermeable reagent into a lumen of an artery, a arteriole, a capillary or a vein in an intact organ or an intact animal to react the cell membrane impermeable reagent with a molecule expressed on the luminal surface; and (c) isolating the reagent-reacted molecule by contacting with an immobilized avidin or strepavidin molecule and removing substantially all of the non-immobilized molecules.

The invention provides a kit comprising a cell membrane impermeable reagent comprising three domains: (i) a first domain comprising an active moiety capable of covalently and non-specifically binding to a molecule expressed on the luminal surface of a cell lining a perfusible space in situ or in vivo, (ii) a second domain comprising a binding domain, and, (iii) a third domain comprising a disulfide moiety situated between the first and second domains linking the first domain to the second domain; and, printed matter instructing use of the cell membrane impermeable reagent for administration into a lumen of an intact organ or an intact animal to react the cell membrane impermeable reagent with a molecule expressed on the luminal surface to isolate the reagent-reacted molecule. In one embodiment of the kit, the binding domain of the cell membrane impermeable reagent is biotin and the printed matter instructs isolation of the reagent-reacted molecule by contact with an immobilized avidin or strepavidin molecule and removing substantially all of the non-immobilized molecules. In another embodiment, the printed matter instructs administration into a lumen of an artery, a arteriole, a capillary or a vein.

The details of the invention are set forth in the accompanying drawings and the description below. A further understanding of the nature and advantages of the present invention is realized by reference to the remaining portions of the specification, the figures and claims.

All publications, patents and patent applications cited herein are hereby expressly incorporated by reference for all purposes.

DETAILED DESCRIPTION

This invention provides a novel means to label and isolate molecules, particularly polypeptides, which are exposed on the luminal side of cells lining perfusible spaces in a tissue, organ or whole intact organism. These perfusible spaces include, e.g., vascular, ductal, CSF space, peritoneum, eye, fascial spaces, and other perfusible tissue spaces. As discussed above, while the methods of the invention can be used to identity and isolate any lumen exposed molecule, they are particularly well suited for "tagging" or labeling and/or isolating tissue-specific or organ-specific molecules. By utilizing cell membrane impermeable reagents comprising three domains, the methods of the invention can be used to generate a substantially pure preparation of lumen-exposed molecules. The cell membrane impermeable reagents comprise a first domain comprising a chemical moiety capable of covalently and non-specifically binding to a molecule exposed on the luminal surface of a cell lining a perfusible space in situ or in vivo, a second domain comprising a binding domain (e.g., biotin), and a third domain situated between the first and second domains linking the first domain to the second domain by a cleavable chemical moiety (e.g., a disulfide group), wherein the cleavable chemical moiety will not cleave under in vivo conditions.

In one embodiment, the "tagged" reagent-exposed molecule complex is reacted with a binding domain ligand (e.g., avidin, where the binding domain is biotin), which can be immobilized. In one embodiment, the tissue preparation (e.g., tissue extract or homogenate, or the like) comprising the "tagged" lumen-exposed molecule is first bound to an immobilized binding agent ligand, followed by washing away of non-bound molecules (e.g., substantially all non-bound molecules). Because the chemical moiety can be cleaved under conditions wherein no or an insignificant amount of binding domain is separated from its ligand, the methods of the invention can generate preparations comprising no or insignificant amounts of contaminating "non-lumen-exposed" molecules (including, e.g., naturally biotinylated molecules).

For example, as demonstrated in Example 2, the methods of the invention allow preparations of lumen-exposed molecules without contamination by non-lumen-exposed naturally biotinylated polypeptides. Example 1 demonstrates that the methods of the invention can specifically isolate a tissue-specific vascular lumen-exposed polypeptide. These data demonstrate that the methods of the invention can be used to isolate vascular lumen-exposed plasma membrane proteins. Thus, the methods of the invention are capable of distinguishing proteins exposed on the luminal surface of the vasculature from all other proteins present in tissues. While this data used an art-accepted rat animal model, the methods of the invention are applicable to any animal or human system.

DEFINITIONS

Unless defined otherwise, all technical and scientific terms used herein have the meaning commonly understood by a person skilled in the art to which this invention belongs. As used herein, the following terms have the meanings ascribed to them unless specified otherwise.

The term "avidin" as used herein means any biotin-binding compound such as avidin, streptavidin, any modified or mutant avidin produced by laboratory techniques which is capable of binding biotin or a functional equivalent of biotin, any compound designed to function like avidin, and equivalents thereof. See, e.g., Green (1970) Methods Enzymol. 18A:418–424; Green (1965) Biochem. J. 94:23c–24c; Schray (1988) Anal. Chem. 60:853–855; Mock (1985) Analytical Biochem. 151:178–181; Ding (1999) Bioconjug. Chem. 10:395–400; U.S. Pat. No. 6,022,951.

The term "binding domain" means any molecular entity for which there is a ligand, as described in further detail, below.

The term "biotin" as used herein means biotin, any modified biotin, and also includes biotin analogs and equivalents thereof, e.g., biotin methyl ester, desthiobiotin, diaminobiotin or 2-iminobiotin. See, e.g., Hofmann (1982) Biochemistry 21:978–984; Reznik (1998) Proc. Natl. Acad. Sci. USA 95:13525–13530; Torreggiani (1998) Biospectroscopy 4:197–208.

The term "cell membrane impermeable reagent" as used herein means a reagent that cannot enter or pass through the lipid bilayer of a cell membrane; e.g., the cell membrane impermeable reagents of the invention, when perfused into tissue spaces, will only bind to molecules exposed to the lumen of the space (assuming the membranes of the cells lining the lumen are intact).

The term "an intact organ" as used herein means an organ, or a section or piece thereof, whose basic anatomical architecture is intact, e.g., its vasculature (e.g., venules, arterioles, capillaries, lymph) or sinus spaces or the like have not been disrupted such that perfusion of a cell membrane impermeable reagent into the lumen of the vessel or sinus (or other perfusible space) will only label lumen-exposed molecules.

As used herein, "isolated," when referring to a molecule or composition, such as, e.g., an isolated cell membrane impermeable reagent or tissue- or organ-specific a molecule, means that the molecule or composition is separated from at least one other compound, such as a protein, DNA, RNA, lipid, carbohydrate, or other contaminants with which it is associated in vivo or in its naturally occurring state. Thus, a tissue- or organ-specific molecule is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined, e.g., using any analytical chemistry technique, as described herein.

The term "labeling domain" means any molecular entity for which can be detected, as described in further detail, below.

The phrase "a ligand having affinity for the binding agent" as used-herein means any ligand that specifically binds to the "binding agent," i.e., that the binding agent has sufficient affinity for the ligand that it is not non-specific binding. The amount of affinity necessary to be "specifically bound" can be determined functionally, e.g., there is sufficient affinity between an immobilized ligand and a soluble binding agent such that substantially all of the contaminants can be washed away before elution.

The term "luminal surface" as used herein means the surface of any perfusible space, e.g., the lumen-exposed surface of cells lining a perfusible space, e.g., endothelial cells in a vascular space (e.g., the lumen of an artery, vein, capillary, sinus, and the like).

The term "organ specific molecule" or "tissue specific molecule" expressed on a luminal surface of a perfusible space in situ or in vivo means any molecule, e.g., polypeptide, lipid, carbohydrate, expressed on one subset of individual cells (e.g., hematopoietic cells), or tissues (e.g., muscles, skin), or organs (e.g., liver, lung, heart, brain), or groups of organs (e.g., all nervous or digestive tract tissues or organs) and not on another. Organ specific molecules and tissue specific molecules also include normal versus pathological sets of cells, e.g., as with tumor specific antigens. Organ specific molecules and tissue specific molecules also include developmentally distinct phenotypes, e.g., angiogenic blood vessels express different polypeptides on the luminal surfaces of their endothelium than "resting" (non-growing) blood vessels. Thus, targeting of angiogenic blood vessel-specific polypeptides identified by the methods of the invention can be very useful in the treatment of growing tumors.

The term "perfusible space" means any tissue or organ space that can be perfused with a cell-impermeant reagent-containing buffer of the invention, e.g., any vascular or lymphatic lumen, the CSF space, lumens of ducts, vitreous-aqueous humor space of the eye, fascial planes, and the like, including spaces only present under disease, inflammatory or other conditions, e.g., cysts, tumors, and the like.

General Techniques

The invention can be practiced in conjunction with any method or protocol known in the art and described in the scientific and patent literature. The various compositions (e.g., natural or synthetic compounds, polypeptides, peptides, nucleic acids, and the like) used to practice this invention can be isolated from a variety of sources, genetically engineered, amplified, and/or expressed recombinantly. Alternatively, these compositions (e.g., any or all domains of the membrane impermeable reagents of the invention) can be synthesized in vitro by well-known chemical synthesis techniques, as described in, e.g., Organic Syntheses Collective Volumes, Gilman et al. (Eds) John Wiley & Sons, Inc., NY; Venuti (1989) *Pharm Res.* 6:867–873; Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Beaucage (1981) Tetra. Lett. 22:1859; U.S. Pat. No. 4,458,066.

Techniques for the manipulation and isolation of organs, tissues, cells, nucleic acids, polypeptides are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Cell Membrane Impermeant Reagents

This invention provides methods using cell membrane impermeable reagents to label and isolate molecules, particularly polypeptides, exposed on the luminal side of perfusible spaces. The cell membrane impermeable reagents have at least three domains: a first domain comprising a chemical moiety capable of covalently and non-specifically binding to a molecule expressed on the luminal surface of a cell lining a perfusible space in situ or in vivo; a second domain having a binding domain; and, a third domain situated between the first and second domains linking the first domain to the second domain by a cleavable chemical moiety, wherein the cleavable chemical moiety will not cleave under in vivo or physiologic (or equivalent) conditions and can be cleaved under relatively mild conditions.

Moieties Capable of Covalent and Non-Specific Binding to Luminal Molecules

The first domain of the cell membrane impermeable reagent comprises a chemical moiety capable of covalently and non-specifically binding to a molecule expressed on the luminal surface of a cell lining a perfusible space in situ or in vivo. The moiety can be reactive to, e.g., amine, carboxyl, carbohydrate or sulfhydryl groups on the luminally-expressed molecule. The chemistry and reagents for such reactions are well known in the art; see, e.g., catalog of Pierce Chemicals (Rockville, Ill.); www.piercenet.com.

Chemical moiety capable of covalently and non-specifically binding lumen-exposed molecules include amine reactive moieties, e.g., sulfo-NHS ester groups. They react to form a stable covalent bond with amine groups at a pH of about 7 to 9. Such exemplary membrane impermeable cross-linking reagents (which are cleavable) include: thiobis (sulfosuccinimidyl) proprionate groups or sulfosuccinimidyl suberate (see, e.g., Conrad (1985) Int. Arch. Allergy Appl. Immunol. 77:228–231); sulfosuccinimidyl-2-(biotinamido) ethyl-1,3-dithiopropioate, e.g., Sulfobiotin-X-NHS™, catalog 21331T, Pierce Chemicals. These compounds can be designed to be cleavable under mild reducing conditions, using, e.g., dithiothreitol (DTT); mild conditions being, e.g., 10 mg/ml, pH 9, RT). See also, e.g., Shimkus (1985) Proc. Natl. Acad. Sci. 82:2593–2597; Duhamel (1985) J. Histochem. Cytochem. 33:711–714; Gottardi (1995) Am. J. Physiol. 268: F285–F295; Soukup (1995) Bioconjugate Chemistry 6: 135–138.

Other useful chemical moieties capable of covalently and non-specifically binding lumen-exposed molecules are consumable catalysts, e.g., crosslinking agents such as carbodiimide or carbamoylonium (see, e.g., U.S. Pat. Nos. 4,421,847; 4,877,724). With these crosslinking agents, one of the reactants must have a carboxyl group and the other an amine or sulfhydryl group. The crosslinking agent first reacts selectively with the carboxyl group, preferably a carboxyl group on a protein, then is split out during reaction of the "activated" carboxyl group with an anine on the cross-linking reagent, to form an amide linkage between the protein and crosslinking agent, thus covalently bonding the two moieties. See, e.g., U.S. Pat. No. 5,817,774.

Alternatively, sulfhydryl reactive moieties can be used, e.g., maleimide reactive groups such as N-(4-carboxycyclohexylmethyl)maleimide groups can acylate in aqueous or organic media within 2 minutes at room temperature. Maleimide reacts with —SH groups at pH 6.5 to 7.5, forming stable thioether linkages. See, e.g., U.S. Pat. Nos. 5,063,109; 5,053,520.

Carbohydrate-binding moieties can also be used, e.g., an oxidized carbohydrate specific hydrazide, such as 4-(4-N-Maleimidophenyl) butyric acid hydrazide hydrochloride and its homologues having 2 to 8 carbon atoms in the aliphatic chain connecting the carbonyl and phenyl groups of the spacer. See, e.g., U.S. Pat. Nos. 6,015,556; 5,889,155.

Binding Domains

In various embodiments, the second domain of the cell membrane impermeable reagent comprises a binding domain. The binding domain can be any chemical moiety having a known ligand that can be manipulated to identify the lumen-expressed molecule or to isolate the molecule. In one embodiment, it is a moiety that has substantially little affinity for most naturally occurring molecules. Alternatively, if the binding domain moiety has significant affinity for naturally occurring molecules, they are present in relatively lesser amounts, or, have less affinity for the binding domain than the ligand chosen to be used in the purification process.

Such detection- and purification-facilitating domains include, but are not limited to, polypeptides and peptides, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.).

In one embodiment, the binding domain is biotin and its immobilized ligand is avidin or streptavidin. While mammalian cells have significant amounts of naturally biotinylated polypeptides (see Example 2, below), the use of cleavable membrane impermeant reagents in the methods of the invention allow for the generation of a substantially pure preparation of lumen-exposed molecules and avoid contamination by naturally biotinylated polypeptides.

Cleavable Chemical Moieties

The third domain of the cell membrane impermeable reagent comprises a cleavable chemical moiety that will not cleave under in vivo conditions. It is a "linking domain" situated between the first and second domains. The membrane impermeant reagents of the invention can comprise any cleavable chemical moiety that will not cleave under in vivo conditions and, if a binding domain is present, that can be cleaved without disrupting the binding of the binding domain to a binding domain ligand; such cleavable chemical moieties are well known in the art. For example, disulfide groups can be used; with exemplary conditions for cleavage including, e.g., at 37° C. with about 10 to 50 mm dithiothreitol (DTT) at pH 8.5 within 30 minutes disulfides are quantitatively cleaved (the disulfides reduced, in this example); or, disulfides also cleaved with, e.g., about 1% to about 5% B-mercaptoethanol (2-ME), or equivalents.

Alternatively, peptide or oligonucleotide domains can be cleaved by addition of enzymes that recognize specific sequences (e.g., restriction enzymes for specific nucleic acid sequences). For example, the cleavable domain can include a cleavable linker sequences cleavable by endopeptidases, such as, e.g., Factor Xa, enterokinase (Invitrogen, San Diego Calif.) plasmin, enterokinase, kallikrein, urokinase, tissue plasminogen activator, clostripain, chymosin, collagenase, Russell's Viper Venom Protease, post-proline cleavage enzyme, V8 protease, thrombin.

Labeling or Detectable Domains

The invention provides methods of labeling a molecule exposed on a luminal surface of a perfusible space in situ or in vivo for its detection (and, if desired, isolation) comprising use of a cell membrane impermeable reagent comprising three domains, wherein the second domain comprises a labeling, or detectable, domain. In one embodiment, the invention also provides methods of isolating an organ-specific or tissue-specific molecules comprising use of cell membrane impermeable reagents comprising four domains, including a detectable, or labeling, domain.

Any composition which is detectable can be used, many of which are well known in the art, including, e.g., various enzymes, prosthetic groups, colorimetric compositions, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin. See, e.g., U.S. Pat. Nos. 6,022,748; 6,007,994. Radioisotopes or radionuclides can be used as label moieties, e.g., Sc, Fe, Pb, Ga, Y, Bi, Mn, Cu, Cr, Zn, Ge, Mo, Tc, Ru, In, Sn, Re, Sr, Sm, Lu, Eu, Dy, Sb, W, Po, Ta or Tl ions. Exemplary radionuclides include H-3, S-35, I-125, I-131, P-32, Y-90, Re-188, At-211, Bi-212 and the like. Fluorescent metal ion can be used, e.g., metals of atomic number 57 to 71; e.g., ions of the metals La, Ce, Pr, Nd, Pm, Sm, Eu, Gd, Tb, Dy, Ho, Er, Tm, Yb, and Lu. In another embodiment, the label can comprise a paramagnetic elements suitable for the use in magnetic resonance imaging (MRI) applications, e.g., elements of atomic number 21 to 29, 43, 44 and 57 to 71, e.g., Cr, V, Mn, Fe, Co, Ni, Cu, La, Ce, Pr, Nd, Pm, Sm, Eu, Gd, Tb, Dy, Ho, Er, Tm, Yb and Lu.

Molecules Exposed to Lumen in Perfusible Spaces

This invention provides methods using cell membrane impermeable reagents to label lumen-expressed molecules in situ or in vivo and, if desired, subsequently isolate these molecules. The invention can isolate any molecule expressed on the luminal side of any perfusible space, e.g., vascular spaces, such as those in the heart (ventricles, atrium), arteries, arterioles, capillaries and veins, ducts of exocrine and endocrine glands. In one embodiment, the methods of the invention are used to label and/or isolate lumen-exposed tissue- or organ-specific molecules. In alternative embodiments, the methods of the invention are used to label and/or isolate lumen-exposed molecules expressed under certain conditions, e.g., at particular stages of development or aging or apoptosis, after exposure to particular hormones or cytokines (e.g., lymphokines) or neurotransmitters, in stressed, injured, inflamed, infected, or diseased tissues, and the like.

Vascular Vessels

In various embodiment, the methods of the invention comprise perfusion, or infusion, cell membrane impermeable reagents into arteries, arterioles, capillaries, sinuses (e.g., as in the liver, placenta) and the like. Such methodologies are well known in the art. For example, aortic arch flush, as in, e.g., Woods (1999) J. Trauma 47:1028–1036; arterial cannula in the supraceliac aorta, as in e.g., Mishima (1999) Ann. Thorac. Surg. 67:874–875; coaxial catheter systems permitting movement in three dimensions, as in, e.g., Lauer (1999) J. Am. Coll. Cardiol. 34:1663–1670; cardiac catheterization by a transhepatic approach as in, e.g., McLeod (1999) Heart 82:694–696; central venous catheterization as in, e.g., Albuquerque (1998) Curr. Opin. Clin. Nutr. Metab. Care 1:297–304; placement of central venous catheters as in, e.g., Cavatorta (1999) Clin. Nephrol. 52:191–193, or Ball (1999) Anaesthesia 54:819, and the like.

Lymphatic Vessels

In various embodiment, the methods of the invention comprise perfusion, or infusion, cell membrane impermeable reagents into lymphatic ducts. Such methodologies are well known in the art, e.g., cannulation as in Chuang (1986) J. Surg. Res. 41:563–568; direct cannulation mediastinal lymphatics as in Leeds (1981) Invest. Radiol. 16:193–200; see also, e.g., Tran (1993) Perit. Dial. Int. 13:270–279.

Epithelium-Lined Perfusible Spaces

In various embodiment, the methods of the invention comprise perfusion, or infusion, cell membrane impermeable reagents into epithelial lined perfusible spaces, such as, e.g., exocrine and endocrine ducts and pores, respiratory epithelium (nasal epithelium, bronchi, lungs, sinuses), cerebral spinal fluid space (CSF) by, e.g., intrathecal administration, digestive tract epithelium (mouth, pharynx, esophagus, stomach, intestines, colon), bladder, and the like.

Formulations for Administration In Situ or In Vivo

The compositions for administration will commonly comprise a buffered solution comprising a cell membrane impermeable reagent in a pharmaceutically acceptable carrier, e.g., an aqueous carrier. A variety of carriers can be used, e.g., buffered saline and the like. These solutions can be sterile, e.g., generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The exact concentration of cell membrane impermeable reagents, and the frequency of administration can also be adjusted by routine determinations.

Routes of Delivery

The cell membrane impermeable reagents can be delivered by any means known in the art systemically (e.g., intravenously), regionally, or locally (e.g., intra- or perituremoral or intracystic injection) by, e.g., intraarterial, intratumoral, intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa), intra-tumoral (e.g., transdermal application or local injection). For example, intraarterial injections can be used to have a "regional effect," e.g., to focus on a specific organ (e.g., brain, liver, spleen, lungs). For example, intrahepatic artery injection can be used to localize delivery of cell membrane impermeable reagents to the liver; or, intracarotid artery injection to localize delivery of cell membrane impermeable reagents to the brain (e.g., occipital artery, auricular artery, temporal artery, cerebral artery, maxillary artery, etc.).

Preparation of Tissues and Organs

This invention provides methods for the labeling and/or isolation of lumen-exposed molecules by perfusing these spaces in situ or in vivo with cell membrane impermeable reagents. Any perfusible space (e.g., vessel, duct, fascia, sinus) in any organ or tissue can be analyzed by the methods of the invention. The reagent-reacted molecule can be isolated by isolation of the perfused organ or tissue (e.g., by dissection) and making a cell or a membrane isolate or a cell or a tissue homogenate preparation or an extract derived from the reagent-reacted tissue or organ or animal. This preparation is then reacted with a ligand having affinity for the binding domain of the cell membrane impermeable reagent.

Cell or tissue homogenates, membrane preparations or cell extracts can be accomplished by any of many known methods in the art.

Analysis of Isolated Molecules

This invention provides methods to isolate molecules (e.g., organ- or tissue-specific polypeptides) exposed on a luminal surface of a perfusible space. These molecules, e.g., carbohydrates, lipids, polypeptides, and the like can be analyzed and quantified by any of a number of general means well known to those of skill in the art. These include, e.g., analytical biochemical methods such as NMR, spectrophotometry, electrospray ionization (e.g., Fourier transform ion cyclotron resonance mass spectrometry; see, e.g., U.S. Pat. No. 6,011,260), radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Kits

The invention provides kits that contain the cell membrane impermeable reagents of the invention in suitable buffers for administration (perfusion) to intact organs, tissues or animals. In one embodiment, the kits also contain printed matter setting forth instructions for practicing the methods of the invention, as set forth herein.

A number of embodiments of the invention have been described. Nevertheless, it will be understood that various modifications may be made without departing from the spirit and scope of the invention. For example, a variety of cleavable chemical moieties, or different binding agents, or different means to randomly bind and covalently bind to cell surface molecules, can be used in the cell membrane impermeant reagents used in the methods of the invention. Accordingly, other embodiments are within the scope of the following claims.

EXAMPLES

The following example is offered to illustrate, but not to limit the claimed invention.

Example 1

Selective Isolation of Polypeptides Expressed in an Organ-Specific Manner on Vascular Endothelium The following example demonstrates that the compositions and methods of the invention can be used to selectively isolate lumen-exposed molecules, such as polypeptides. In particular, this example demonstrates the selective isolation of a vascular endothelium lumen-exposed polypeptides from various organs of a rat, including brain, lungs, kidneys, hearts, liver, and omentum (fat).

In these experiments, male Fisher rats were used. Each rat was anesthetized by injection with 1.6 ml of ketamine:xylazine mixture (7.5 mg/ml ketamine: 5 mg/ml xylazine). A tracheotomy was then performed by inserting a catheter into the trachea of the rat and attaching this to a bulb to provide ventilation. The thorax of the animal was then opened and pericardium removed. 0.5 ml heparin (2000 units/ml) was injected into each of the left and right ventricles. A 14-guage catheter was then attached to a perfusion line and inserted into the left ventricle. Although the amount of pressure was not critical, a range of between about 10 mm Hg and 80 mm Hg was used. Perfusion was at 20 mm Hg; an incision was made to the right atrium to permit flow of the perfusion buffer.

To clear the vasculature of blood, a buffer of 60 ml Ringers at pH 7.5 with nitroprusside at 0.1 mg/ml was perfused. Second, the vasculature was prepared for reaction with the cell membrane impermeant reagent by perfusion with 60 ml of borate-buffered saline at pH 9.0 (pH is not critical, a range of between about 7.5 and about 9.5 can be used with this particular reagent). Third, about 20 ml of this same buffer with the DTT cleavable reagent sulfosuccinimidyl-2-(biotinamido)ethyl-1,3-dithiopropioate (purchased as Sulfobiotin-X-NHS™ from Pierce Chemicals) was injected in the tissue and allowed to react for about one to two minutes (greater times and greater volumes can be successfully used). Concentrations of reagent from about 2 to about 50 mg/ml can also be successfully used to label lumen-exposed molecules.

After the reaction with reagent, 60 ml Ringers at pH 7.5 with 1.8 mg/ml glycine was perfused to remove excess biotin and to quench any remaining activated biotin. pH is not critical, a range of between about 7.5 and about 9.5 can be used. After this wash 60 ml of 0.25 M sucrose, 25 mM HEPES with 10 mg/ml of various protease inhibitors, including leupeptin, pepstatin, E64 and PMSF, to prevent proteolysis (the choice of protease inhibitors or their concentrations is not critical). Organs and tissues were then separately removed and stored at −80° C. until ready for use.

Homogenization was carried out by mincing a known weight of tissue with a razor blade. The minced tissue was placed in ten volumes (v/w) PBS at pH 7.4, 1.0 mM EDTA, 1.8 mg/ml glycine with a cocktail of protease inhibitors, including AEBSF, leupeptin, pepstatin A, bestatin, aprotinin (Sigma Cat. # P8340), E64 and PMSF. This was homogenized in a dounce homogenizer with about ten to twelve up and down strokes at approximately 1500 rpm. The homogenate was then centrifuged in about 20 ml aliquots at 500×g for ten minutes in order to remove cell debris and nuclei. The supernatant was removed and placed in a fresh tube. Each pellet was washed with about ten ml homogenization buffer and the spin repeated. Supernatants were pooled and spun at 40,000×g (or more) for about two hours to pellet the membrane fractions. Each of these pellets was resuspended in about ten ml homogenization buffer and re-homogenized as before. SDS and Triton X-100 detergents were then added to a final concentration of about 1% each to solubilize the cell membranes and release proteins.

These solubilized membrane protein fractions were aliquoted into ten ml aliquots. Thirty of a 50% suspension of strepavidin beads (Pierce Chemicals) at 4-mg/ml binding capacity were added to each tube and this was inverted overnight at room temperature (RT). The beads were then allowed to settle into a pellet and the supernatant discarded. The pellet was washed five times with one ml homogenization buffer, 1% SDS, 1% Triton X-100 in order to remove non-specifically bound protein. Molecules modified with the biotin tag (i.e., the lumen-exposed vascular endothelial polypeptides bound to the membrane impermeable reagent) were specifically eluted from the beads by washing twice in ("mild conditions") 50 ml homogenization buffer with 50 mM DTT, 1% SDS, 1% Triton-X 100; the DTT cleaved the internal disulfide domain of the membrane impermeable reagent, releasing the lumen-exposed vascular endothelial polypeptides and leaving the biotin bound to the immobilized streptavidin.

The eluted proteins were then precipitated with four volumes methanol, one volume chloroform and three volumes water, with mixing after each addition. The solution was centrifuged at 14,000 rpm for five min to separate the phases. The upper phase was removed and three volumes of methanol was added. The solution was centrifuged again to repellet the protein. The pellets were then resuspended in "sample buffer" comprising 83 mM Tris HCl, pH 6.8, 1% 2-mercaptoethanol (2-ME), 2% SDS, 10% glycerol, and boiled for five minutes ("harsh conditions"), after which the sample were ready for reducing polyacrylamide gel electrophoresis (PAGE).

Each preparation (pellet boiled in sample buffer) was separated by PAGE on a 4 to 20% gradient gel (Novex). The electrophoresed polypeptides were then transferred to nitrocellulose by blotting at 25 milliamp overnight. Filters were blocked with 2% BSA in TBS, 0.1% Tween-20 buffer for about one hour at RT. The primary antibody was then added in 0.2% BSA buffer for about one hour at RT. The filters were washed three times for about ten min in TBS-TWEEN and then incubated with the "secondary" horse radish peroxidase (HRP)-labeled antibody. After washing three times, the blots were developed with ECL-Plus™ (Amersham/Pharmacia) and photographed over UV light.

Histologic analysis was also performed on the tissue sections. Prior to freezing of the perfused and isolated organs and tissues, a small cube (approximately one cm cubed) was cut off for histologic analysis. While the tissue section can be prepared by any known technique, in this case the cube was placed in tissue embedding medium (HistoPrep™, Fisher), in a small plastic cube. This was then immersed for about twenty seconds in 2-methylpentane which had been prechilled in liquid nitrogen. The frozen cubes were kept on dry ice until they were sectioned. The tissues were sectioned at five mm slices on a cryostat, air dried overnight and fixed in acetone for two min. Fluorescent tags could be examined directed from these sections (using a fluorescent microscope).

For the in vivo localization studies, 0.5 ml biotin-labeled antibody at one mg/ml was injected into the tail vein of a rat under light anesthesia. The antibody was allowed to circulate for about thirty min after which time the animal was sacrificed and its organs removed individually. Sections of each were made as described above. The slides were stained with streptavidin-HRP using standard immunohistochemical techniques to detect the presence of antibody.

A rat was perfused with fluorescein-linker NHS (Pierce Chemical) at 1 mg/ml. A second rat was removed perfused with buffer only as negative control. Following perfusion, the organs were removed and tissue sections were made of each. Localization of the fluorescein to the vascular lumen without penetrating into the tissue was confirmed by fluorescence microscopy. Capillaries from kidneys from the two rats (test and control) were compared (capillaries were also viewed by phase contrast microscopy). When viewed by fluorescence microscopy, the capillary in the buffer-perfused animal is no longer visible, since there is no fluorescent label bound to endothelium. In contrast, in the animal perfused with the fluorescein-linker NHS, the capillary is readily seen because of binding of the reagent to the lumen-exposed endothelium (the NHS-moiety binds non-specifically to lumen-exposed polypeptides). Because the reagent is membrane impermeable, the fluorescein is viewed as lining the walls of the capillaries; no fluorescence is viewed in the tissue surrounding the vessel.

Figure 1:
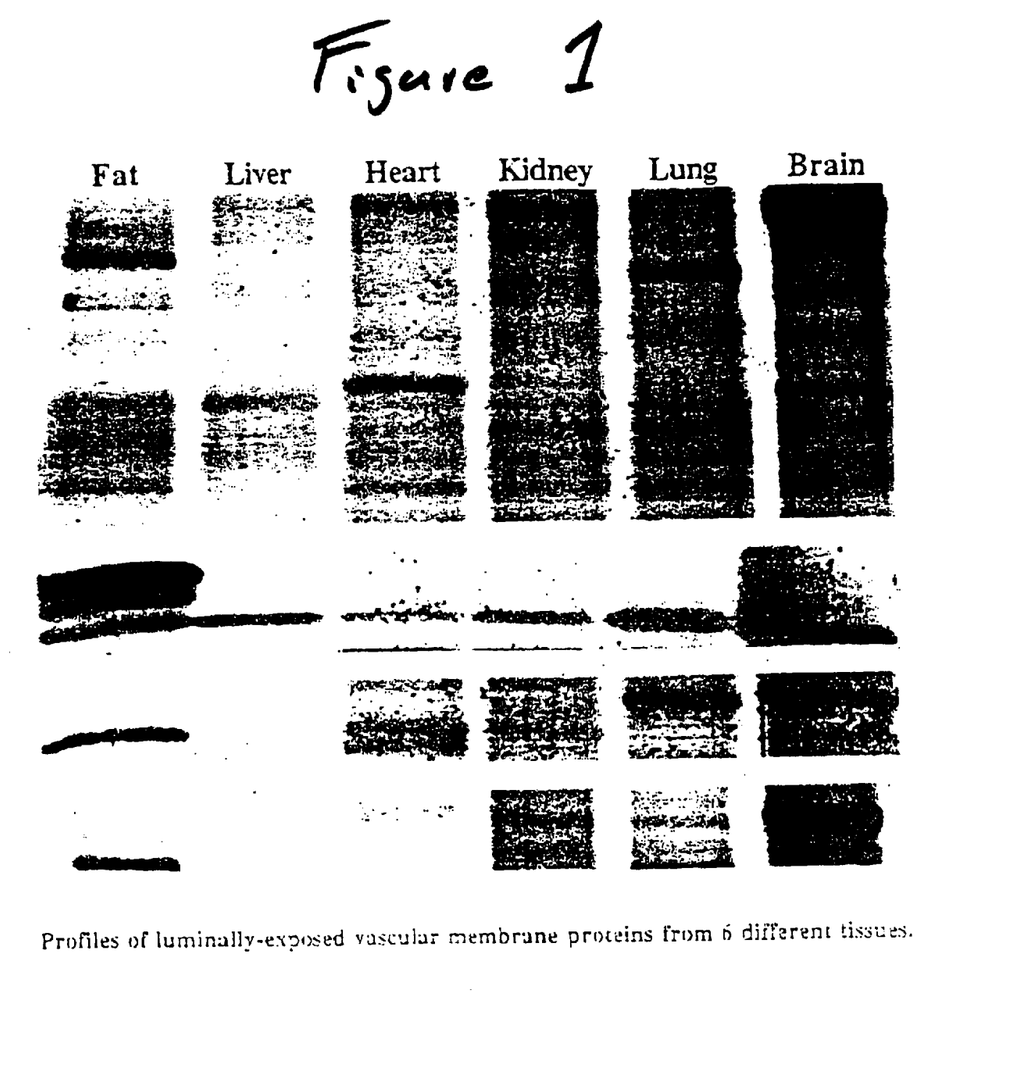
FIG. 1 shows a representation of a stained polyacrylamide gel electrophoresis (PAGE) separating lumen-exposed molecules from rat brains, lungs, kidneys, hearts, liver and fat, isolated using an exemplary method of the invention, as described in Example 1, below.

As described above, rats were perfused with the DTT-cleavable reagent sulfosuccinimidyl-2-(biotinamido)ethyl-1,3-dithiopropioate. The reagent had an in situ incubation time averaging about one and a half min. Organs were removed and tissue homogenized and lumen-exposed molecules isolated as described above. The isolated lumen-exposed molecules from ten brains (14 grams total), three lungs (five grams total), four kidneys (six grams total), four hearts (six grams total), five grams of liver and five grams of omentum (fat) were analyzed/isolated on a 4 to 20% gradient PAGE (1.5 hours at 150 volts). The resulting gel was stained with Gelcode Blue™ stain (Pierce Chemical) to visualize the polypeptides from the different organs separated on the PAGE, as shown in FIG. 1. As demonstrated by the stained gel, lumen-exposed organ-specific vascular membrane polypeptides can be directly visualized on the PAGE. Vascular membrane proteins specific for a given tissue or a limited number of tissues are readily visualized, and isolated, by this technique.

Figure 2:
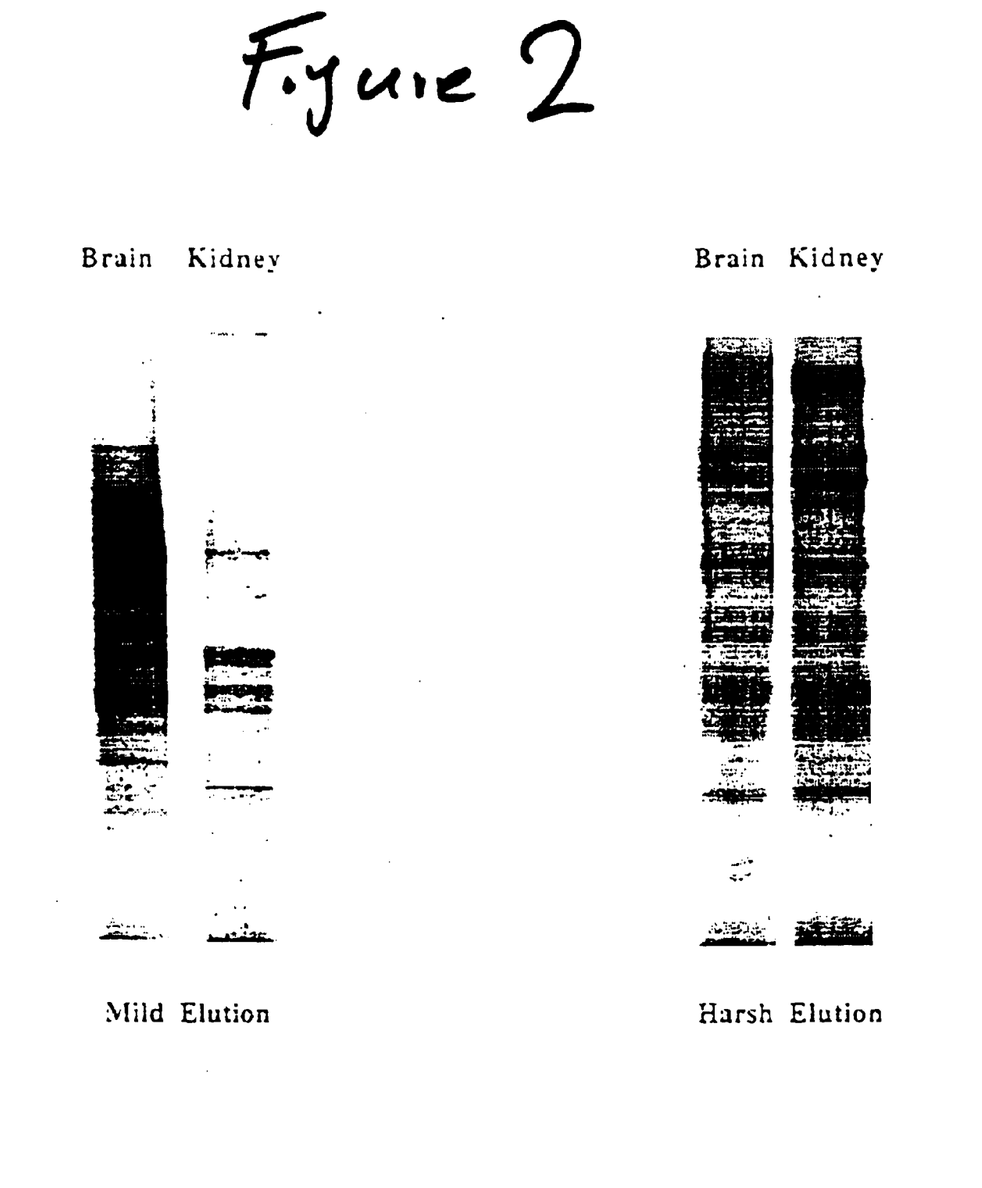
FIG. 2 shows a representation of a stained PAGE separating polypeptides eluted from beads under both "mild conditions" (left panel) (i.e., an exemplary method of the invention) and "harsh conditions" (right panel); harsh conditions being boiling in a sample buffer as described in Example 1, below.

To demonstrate the presence of potential contaminating naturally biotinylated proteins still bound to the immobilized binding domain ligand (in this case, immobilized strepavidin), the beads (after cleaving of the cleavable domain and elution of the cleaved half of the membrane impermeant reagent containing the lumen-exposed molecule) were eluted under "harsh conditions," i.e., boiled in sample buffer (described above). This treatment will wash off all molecules remaining bound to the immobilized streptavidin. These samples were separated by PAGE and the gel stained (as above), the results of which are shown in FIG. 2. These results demonstrate that there are significant amount of proteins (i.e., naturally biotinylated proteins and non-specifically bound polypeptides not eluted under "mild conditions") remaining on the beads after reduction of the membrane impermeable reagent's disulfide moiety (the "cleavage domain") and subsequent "mild conditions" elution off of the non-immobilized fraction. These results also demonstrate that the PAGE polypeptide profile of the second "harsh" elution (including the naturally biotinylated proteins) is significantly different from the profile of the first "mild" elution fraction, i.e., the fraction comprising substantially only lumen-exposed vascular endothelial polypeptides.

These results further demonstrate that the profiles obtained under mild conditions reveal significant differences between tissues, while profiles of proteins remaining on the matrix subsequently eluted using harsh conditions are nearly identical between tissues. Thus, tissue-specific differences will only be revealed using mild conditions that specifically elute labeled proteins while leaving contaminants bound to the matrix (these contaminants are eluted using harsh conditions). These results also demonstrate that the methods of the invention can generate a preparation substantially free of "contamination" by naturally biotinylated polypeptides. Use of a membrane impermeable reagent lacking a cleavable domain would not allow discrimination between labeled ("tagged") lumen-exposed vascular proteins and contaminating biotinylated proteins.

Figure 3A:
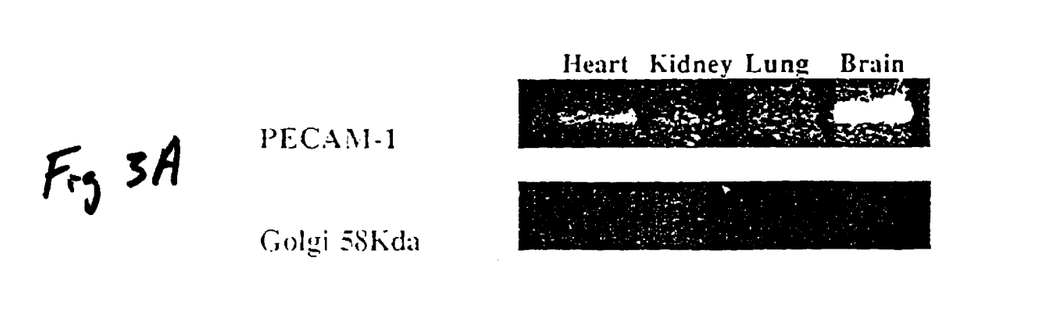
FIG. 3A shows a representation of the results of a Western blot of a PAGE separating vascular lumen-exposed polypeptides, prepared by the methods of the invention, stained with an antibody that recognizes a polypeptide that is only expressed on the lumen of vascular endothelial cells (PECAM-1) and an antibody that recognizes a polypeptide only expressed intracellularly (the Golgi 58 kDa polypeptide), as described in Example 1, below.
Figure 3B:
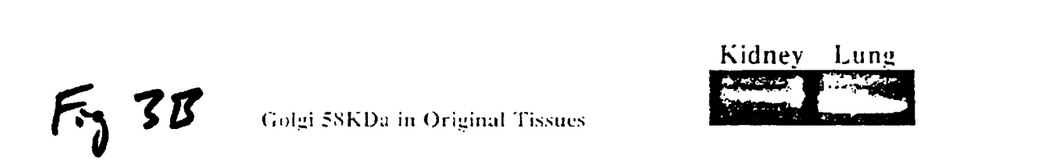
FIG. 3B shows a Western blot of total tissue homogenate stained with anti-Golgi 58 kDa polypeptide antibody.

To establish the purity of the membrane preparations, Western blots were carried out for proteins known to be lumen-exposed endothelial plasma membrane associated polypeptides and for polypeptides known to be expressed on membranes elsewhere in tissues. PECAM-1 (also known as CD31, or endoCAM) was selected for analysis because it is a molecule known to be expressed on the plasma membrane of endothelial cells and exposed to the lumen of blood vessels (see, e.g., U.S. Pat. No. 5,955,4430; Wakelin (1996) J. Exp. Med. 184:229–239). It should, therefore, be labeled and isolated by the methods of the invention. In contrast, the Golgi-expressed 58K polypeptide should not be seen in any of these fractions (see, e.g., Bashour (1998) J. Biol. Chem. 273:19612–19617). Lumen-exposed polypeptides isolated using the methods of the invention (from the rat heart; kidney, lung and brain organ preparations, as described above) were separated by PAGE and stained, as described above. As is demonstrated by the Western blot represented in FIG. 3A, rat heart, kidney, lung and brain preparations contained significant amounts of PECAM-1, while the same fractions contained no Golgi-expressed 58K polypeptide, These results further demonstrate that the isolation process of the invention is specific for lumen-exposed (in this case, vascular endothelium exposed) molecules.

To demonstrate that the methods of the invention can specifically isolate a known vascular lumen-exposed polypeptide, a Western blot (containing separate, lumen-exposed protein preparations from several rat organs, as described above) was carried out using the OX-26 monoclonal antibody (Accurate), which is specific for CD71, the transferrin receptor (see, e.g., U.S. Pat. No. 6,004,814), a polypeptide known to be expressed on vascular endothelial cells in the brain. The results demonstrated that the CD71 polypeptide recognized by the OX-26 antibody is expressed only in the brain preparation and not in the heart, kidney or lung preparations. In vivo labeling studies with anti-CD71 antibody confirmed that CD71 is only expressed in brain capillaries. OX-26 and an isotype (negative) control antibody were labeled with biotin. Each antibody was injected into separate rats (0.5 ml at 1 mg/ml) and allowed to circulate for about 30 min. Immunohistochemical staining of tissue sections revealed that the anti-CD71 antibody had localized to (i.e., bound specifically to, above background) the brain capillaries and did not specifically bind to capillaries in other organs or tissues. The isotype control did not localize to any tissue (no binding above background). Thus, these results also demonstrate that the methods of the invention can specifically isolate a tissue-specific vascular lumen-exposed polypeptide.

Example 2

Methods of the Invention Exclude the Significant Amounts of Naturally Biotinylated Polypeptides The following example demonstrates that the methods of the invention, by using reagents which are cleavable under mild conditions, are superior to techniques which use non-cleavable reagents. This example demonstrates the advantages of the methods of the invention, which use a cell membrane impermeable reagent comprising a domain situated between, a first polypeptide-reactive domain and a second biotin-comprising domain, wherein this third domain links the first domain to the second domain by a cleavable chemical moiety that will not cleave under in vivo conditions, but can be induced to cleave under defined "mild conditions." Thus, rather than using the harsh conditions needed to elute biotin from its ligand (avidin or streptavidin) to separate the "tagged" lumen-exposed polypeptide from the immobilized fraction, the "tagged" lumen-exposed molecules can be eluted by cleaving the reagent under "mild conditions."

As demonstrated below, the harsh conditions needed to elute non-cleavable reagents resulted in significant amounts of "contaminating" compositions in the eluate in the form of naturally biotinylated proteins (including, significantly, those not exposed to the lumen in vivo). Thus, use of non-cleavable "tagging" reagents made it impossible to selectively identify and isolate tagged lumen-exposed compositions.

Methods which use non-cleavable cell membrane impermeable reagents, e.g., as described, e.g., by De La Fuente (1997) Amer. J. of Physiol. 272:L461-L470, must use harsh conditions to separate the biotinylated polypeptide from the immobilized avidin. De La Fuente "tagged" lumen-exposed polypeptides in lungs by perfusing the pulmonary artery with the cell membrane impermeant, non-cleavable biotinylated reagent sulfosuccinimidyl 6-biotin-amido hexanoate, which labels amine groups of polypeptides. De La Fuente incubated reagent-reacted tissue homogenates with strepavidin-agarose beads. However, because the affinity between biotin and avidin is relatively strong (e.g., about $10^{-15}$ $M^{-1}$), to elute the biotinylated polypeptides from the strepavidin beads, harsh conditions had to be used as elution conditions. This resulted in significant amounts of "contamination" (i.e., non-lumen-exposed compositions) in the eluate in the form of non-specifically binding compositions, e.g., polypeptides and other molecules. In contrast, the methods of the invention, by using cleavable cell membrane impermeant reagents, can be used to make preparations of lumen-exposed molecules with significantly less "contamination" by naturally biotinylated compositions.

Materials and Methods:

These experiments were performed using essentially the same materials, reagents and protocols as described above; male Fisher rats were also used.

Figure 4:
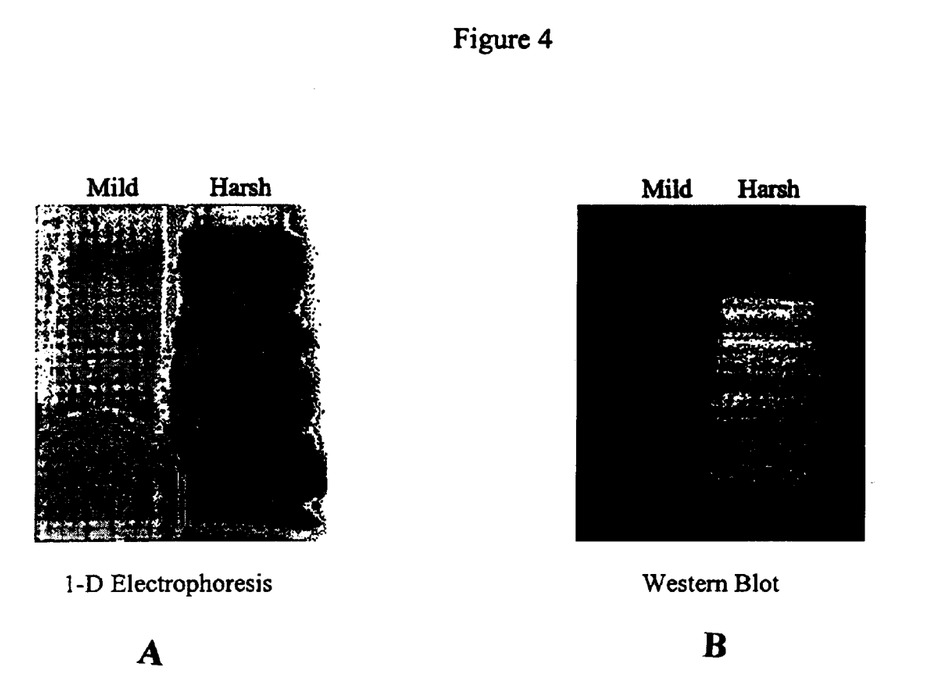
FIG. 4 shows a representation of the results of a protein stained PAGE (FIG. 4A) and a Western blot of this gel probed with a streptavidin-fluorescent probe (FIG. 4B), as described in detail in Example 2. Streptavidin beads added to membrane preparation to purify naturally biotinylated proteins were first eluted using "milder" elution conditions (left lanes of FIGS. 4A and 4B); followed by elution under "harsh conditions" (right lanes of FIGS. 4A and 4B), as described in Example 2.

Results:

Rat livers perfused with buffer only were removed and homogenized. Membranes were isolated. Streptavidin beads were added to the membrane preparation to purify naturally biotinylated proteins. Streptavidin beads were added to the membrane preparation to purify naturally biotinylated proteins. In one experiment the beads were eluted using "milder" elution conditions and the eluted fraction analyzed by one-dimensional electrophoresis (PAGE) and Western blot, as shown in the left panels of FIGS. 4A and 4B. As demonstrated by this analysis, elution under mild conditions isolated virtually no "contaminating" proteins. Similarly, when this same buffer is used to cleave the immobilized cell membrane impermeant reagent and elute the "tagged" polypeptide in the methods of the invention, substantially all of the eluted proteins with be those bound to the reagent via the first domain, with "contaminating" naturally biotinylated polypeptides remaining bound to the immobile fraction.

In contrast, under conditions required to elute biotin from avidin, significant amounts of "contaminating" naturally biotinylated polypeptides were eluted. In another experiment, the beads were treated ("eluted") by boiling in "harsh conditions," as described above. Analysis by PAGE and Western blot, as shown in the right panels of FIGS. 4 and 4B, demonstrated that under harsh conditions many contaminating proteins eluted from the beads. The presence of these "naturally biotinylated" proteins makes it impossible to selectively isolated lumen-exposed molecules under harsh elution conditions.

Figure 5:
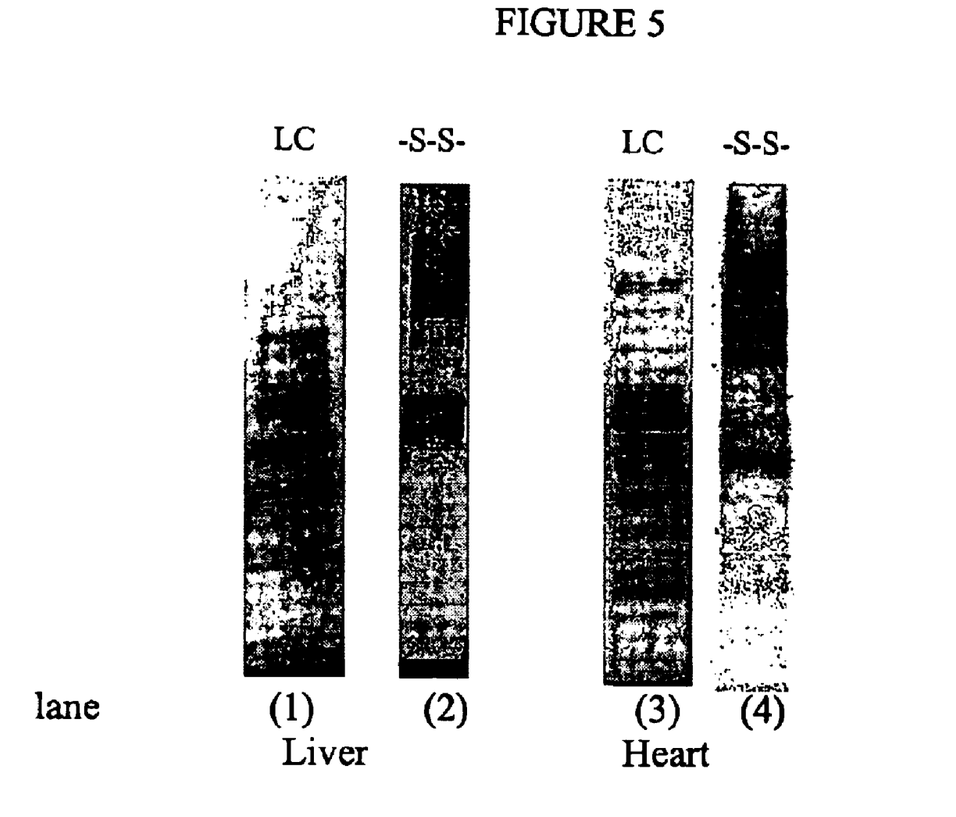
FIG. 5 shows a representation of the results of a protein stained PAGE comparing harsh elution conditions with LC-Biotin versus mild elution conditions with -S-S-biotin for the elution of proteins from liver and heart preparations, as described in Example 2.

Next, experiments were performed comparing the ability of sulfosuccinimidyl 6-biotinamido hexanoate (a non-cleavable membrane impermeable reagent, designated "LC" in FIG. 5) and a cell membrane impermeable reagent used in methods within the scope of the invention (sulfosuccinimidyl-2-(biotinamido)ethyl-1,3-dithiopropioate, designated as "-S-S-" in FIG. 5 (purchased as Sulfobiotin-X-NHS from Pierce Chemicals), with a DTT cleavable domain) were directly compared (using essentially the same materials, reagents and protocols as described above (in Example 1). The two reagent were perfused into intact animals and membranes from liver and heart were prepared, as described above. Both membrane preparations were reacted with bead-immobilized avidin. After several washings, each batch of beads was (first) eluted under "mild conditions" comprising 50 mM DTT, 1% SDS, 1% Triton-X 100. The beads were next eluted under "harsh conditions" (83 mM Tris HCl, pH 6.8, 1% 2-mercaptoethanol (2-ME), 2% SDS, 10% glycerol, and boiled for five minutes). The eluted proteins were separated by PAGE and stained (as described above); a representation of these gels is presented as FIG. 5.

The profiles of eluted proteins isolated with the two reagents were found to be significantly different (equal protein loads were used in each PAGE lane to allow comparison of the two reagents). Elution of beads reacted with sulfosuccinimidyl-2-(biotinamido)ethyl-1,3-dithiopropioate tagged samples under mild conditions showed no staining over background (expected results because mild conditions cannot elute the high affinity bond between biotin and avidin or streptavidin and the fact that this reagent has no cleavable domain). The samples were next eluted under "harsh conditions" and the eluates analyzed; FIG. 5, lanes 1 and 3, for liver and heart, respectively.

Elution of beads reacted with the cleavable reagent Sulfobiotin-X-NHS™ under mild conditions is shown as lanes 2 and 4, for liver and heart, respectively. As can be seen, the profiles of eluted proteins isolated with the two reagents are significantly different. This can be explained by significant levels of background when using harsh elution conditions (lanes 1 and 3) due to the presence of endogenously biotinylated proteins and the fact that proteins that non-specifically interact with the matrix (i.e., immobilized avidin beads) are eluted under harsh conditions. These results further demonstrate the superiority of the methods of the invention to isolate lumen-exposed molecules.

What is claimed is:

1. A method of identifying a protein exposed on a luminal surface of a cell lining of a perfusible space in situ or in vivo comprising the following steps:
   (a) providing a cell membrane impermeable reagent comprising three domains
      (i) a first domain comprising a chemical moiety capable of covalently and non-specifically binding to the protein exposed on the luminal surface of a cell lining of a perfusible space in situ or in vivo,
      (ii) a second domain comprising a labeling domain, and
      (iii) a third domain situated between the first and second domains linking the first domain to the second domain by a cleavable chemical moiety, wherein the cleavable chemical moiety comprises a disulfide group, a periodate-cleavable glycol, a dithionite-cleavable diazobond, a hydroxylamine-cleavable ester, or a base-labile sulfone;
   (b) administering the membrane impermeable reagent into the perfusible space in an intact organ or an intact animal to react the cell membrane impermeable reagent with proteins exposed on the luminal surface of the cell lining of the perfusible space to label the lumen-exposed protein; and
   (c) identify a lumen exposed protein under a condition that does not denature the protein.

2. The method of claim 1, wherein the reagent-reacted lumen-exposed protein is an organ-specific or a tissue-specific protein.

3. The method of claim 1, wherein the perfusible space is a lumen of a vascular vessel and the cell lining the space is an endothelial cell.

4. The method of claim 3, wherein the vascular vessel is an artery, an arteriole, a vein, or a capillary.

5. The method of claim 1, wherein the perfusible space is a lumen of a cerebral spinal fluid (CSF) space.

6. The method of claim 1, wherein the perfusible space is a lumen of a lymphatic vessel and the cell lining the space is an endothelial cell.

7. The method of claim 1, wherein the perfusible space is a lumen of an endocrine or exocrine duct or pore.

8. The method of claim 1, wherein the cell lining the perfusible space is an epithelial cell.

9. The method of claim 1, wherein the organ is, or the tissue is derived from, a heart, a lung, a brain, a liver, a kidney, an endocrine gland, skin, a reproductive organ, a digestive tract organ, or an eye.

10. The method of claim 1, wherein the labeling domain of the reagent is selected from the group consisting of an enzyme, biotin, a colorimetric moiety, a fluorescent moiety, a luminescent moiety, a bioluminescent moiety, a radionucleotide and a paramagnetic element.

11. The method of claim 10, wherein the enzyme is selected from the group consisting of horseradish peroxidase, alkaline phosphatase, β-galactosidase, and acetylcholinesterase.

12. The method of claim 10, wherein the bioluminescent moiety is selected from the group consisting of luciferase, luciferin, and aequorin.

13. The method of claim 10, wherein the radionucleotide is selected from the group consisting of H-3, S-35, I-125, I-131, P-32, Y-90, Re-188, At-211, and Bi-212.

14. The method of claim 10, wherein the paramagnetic moiety is selected from the group consisting of Cr, V, Mn, Fe, Co, Ni, Cu, La, Ce, Pr, Nd, Pm, Sm, Eu, Gd, Tb, Dy, Ho, Er, Tm, Yb, and Lu.

15. The method of claim 10, wherein the fluorescent moiety is selected from the group consisting of umbelliferone, fluorescein, fluorescein isothiocyanate, rhodamine, dichlorotriazinylamine fluorescein, dansyl chloride, and phycoerythrin.

16. The method of claim 1, wherein the cleavable chemical moiety comprises a disulfide group.

17. The method of claim 1, wherein administering the cell membrane impermeable reagent into the perfusible space of the intact organ or tissue or the intact animal comprises administration of a buffered, aqueous solution comprising the cell membrane impermeable reagent.

18. A method of isolating a protein that is exposed on a luminal surface of a perfusible space comprising the following steps:
 (a) providing a cell membrane impermeable reagent comprising three domains
  (i) a first domain comprising a chemical moiety capable of covalently and non-specifically binding to a protein expressed on the luminal surface of a cell lining a perfusible space in situ or in vivo,
  (ii) a second domain comprising a binding domain;
  (iii) a third domain situated between the first and second domains linking the first domain to the second domain by a cleavable chemical moiety, wherein the cleavable chemical moiety comprises a disulfide group, a periodate-cleavable glycol, a dithionite-cleavable diazobond, a hydroxylamine-cleavable ester, or a base-labile sulfone;
 (b) administering the cell membrane impermeable reagent into the perfusible space in an intact organ or an intact animal to react the cell membrane impermeable reagent with a protein expressed on the luminal surface of the cell lining of the perfusible space; and
 (c) isolating the reagent-reacted lumen-exposed protein by contacting the reagent-reacted lumen-exposed protein with a ligand; and
 (d) identify a lumen exposed protein under a condition that does not denature the protein.

19. The method of claim 18, wherein the lumen-exposed protein is an organ-specific or a tissue-specific protein.

20. The method of claim 19, further comprising the step of comparing the reagent-reacted proteins from different organs or tissues to identify the organ-specific or tissue-specific protein, wherein the organ-specific or tissue-specific protein is exposed on the luminal surface of the perfusible space of only one of the compared organs or tissues.

21. The method of claim 18, wherein the perfusible space is a lumen of a vascular vessel and the cell lining the space is an endothelial cell.

22. The method of claim 21, wherein the vascular vessel is an artery, an arteriole, a vein, or a capillary.

23. The method of claim 18, wherein the perfusible space is a lumen of a cerebral spinal fluid (CSF) space.

24. The method of claim 18, wherein the perfusible space is a lumen of a lymphatic vessel and the cell lining the space is an endothelial cell.

25. The method of claim 18, wherein the perfusible space is a lumen of an endocrine or exocrine duct or pore.

26. The method of claim 18, wherein the cell lining of the perfusible space is an epithelial cell.

27. The method of claim 18, wherein the organ is, or the tissue is derived from, a heart, a lung, a brain, a liver, a kidney, an endocrine gland, skin, a reproductive organ, a digestive tract organ, or an eye.

28. The method of claim 18, wherein the ligand comprises of biotin.

29. The method of claim 18, wherein the ligand comprises a polypeptide, a nucleic acid, or a peptide nucleic acid.

30. The method of claim 29, wherein the polypeptide comprises a polyhistidine, a protein A domain, or a FLAG extension.

31. The method of claim 18, wherein the cleavable chemical moiety comprises a disulfide group.

32. The method of claim 18, wherein administering the cell membrane impermeable reagent into the perfusible space of the intact organ-or tissue or the intact animal comprises administration of a buffered, aqueous solution comprising the cell membrane impermeable reagent.

33. The method of claim 18, wherein two separate cell membrane impermeable reagents are co-administered.

34. The method of claim 18, wherein the reagent-reacted protein is isolated by
 (a) contacting a cell or a membrane isolate or a cell or a tissue homogenate or an extract derived from the reagent-reacted organ or animal with a ligand having affinity for the binding domain of the cell membrane impermeable reagent; and
 (b) removing a non-bound protein from the ligand-bound proteins.

35. The method of claim 34, wherein the ligand is immobilized.

36. The method of claim 35, wherein the ligand is immobilized on a bead.

37. The method of claim 34, wherein the ligand is an avidin or a strepavidin molecule.

38. The method of claim 34, wherein the reagent-reacted protein is further isolated by removing substantially all of the non-bound protein from the ligand-bound proteins.

39. The method of claim 34, wherein the non-bound protein is removed by washing.

40. The method of claim 34, wherein the cleaving step does not dissociate the ligand from the binding domain after removing a non-bound protein.

41. The method of claim 40, wherein the ligand-bound lumen-exposed protein is further isolated by elution from the binding domain and the ligand.

42. A method of isolating an organ-specific or tissue-specific protein that is exposed on a luminal surface of an arteriole, a capillary or a vein comprising the following steps:
   (a) providing a cell membrane impermeable reagent comprising three domains
      (i) a first domain comprising an active moiety capable of covalently and non-specifically binding to a protein expressed on the luminal surface of a cell lining a perfusible space in situ or in vivo,
      (ii) a second domain comprising a biotin binding domain, and
      (iii) a third domain comprising a disulfide moiety situated between the first and second domains linking the first domain to the second domain; and
   (b) administering the cell membrane impermeable reagent into a lumen of an artery, a arteriole, a capillary or a vein in an intact organ or an intact animal to react the cell membrane impermeable reagent with a protein expressed on the luminal surface; and
   (c) isolating the reagent-reacted protein by contacting the reagent-reacted protein with an immobilized avidin or streptavidin molecule; and
   (d) identify a lumen exposed protein under a condition that does not denature the protein.

43. The method of claim 42, further comprising the step of cleaving the cleavable chemical moiety of the cell membrane impermeable reagent under a condition that does not dissociate said immobilized avidin or streptavidin protein from said biotin binding domain.

44. The method of claim 42, further comprising the step of comparing the reagent-reacted proteins from different organs or tissues to identify the organ-specific or tissue-specific protein.

45. The method of claim 44 wherein the organ-specific or tissue-specific protein is detected in only one tissue.

* * * * *